(12) United States Patent
Ichihara et al.

(10) Patent No.: US 9,266,899 B2
(45) Date of Patent: *Feb. 23, 2016

(54) METHOD FOR PRODUCING EPOXY COMPOUND

(71) Applicants: JX Nippon Oil & Energy Corporation, Tokyo (JP); OSAKA UNIVERSITY, Suita-shi, Osaka (JP)

(72) Inventors: Junko Ichihara, Suita (JP); Shunro Yamaguchi, Suita (JP); Atsushi Kameyama, Tokyo (JP); Takashi Suzuki, Tokyo (JP); Takashi Morikita, Tokyo (JP)

(73) Assignees: JX Nippon Oil & Energy Corporation, Tokyo (JP); OSAKA UNIVERSITY, Osaka (JP)

(*) Notice: Subject to any disclaimer, the term of this patent is extended or adjusted under 35 U.S.C. 154(b) by 0 days.

This patent is subject to a terminal disclaimer.

(21) Appl. No.: 14/402,398

(22) PCT Filed: Apr. 26, 2013

(86) PCT No.: PCT/JP2013/062354
§ 371 (c)(1),
(2) Date: Nov. 20, 2014

(87) PCT Pub. No.: WO2013/175935
PCT Pub. Date: Nov. 28, 2013

(65) Prior Publication Data
US 2015/0141676 A1    May 21, 2015

(30) Foreign Application Priority Data

May 22, 2012 (JP) ................. 2012-116388

(51) Int. Cl.
| | | |
|---|---|---|
| C07D 303/00 | (2006.01) |
| C07D 493/04 | (2006.01) |
| C07D 301/12 | (2006.01) |
| B01J 23/30 | (2006.01) |

(52) U.S. Cl.
CPC ............... *C07D 493/04* (2013.01); *B01J 23/30* (2013.01); *C07D 301/12* (2013.01)

(58) Field of Classification Search
CPC ..... C07D 493/04; C07D 301/12; B01J 23/30; B01J 31/34
USPC .......................................... 549/544
See application file for complete search history.

(56) References Cited

U.S. PATENT DOCUMENTS

| 5,430,161 A * | 7/1995 | Brown et al. ................. 549/531 |
| 2010/0113807 A1 | 5/2010 | Ichihara et al. |
| 2015/0094479 A1* | 4/2015 | Ichihara et al. ............... 549/544 |

FOREIGN PATENT DOCUMENTS

| JP | S62-234550 A | 10/1987 |
| JP | 2010-235649 A | 10/2010 |
| WO | 2008093711 A1 | 8/2008 |

OTHER PUBLICATIONS

Int'l Search Report issued Jun. 11, 2013 in Int'l Application No. PCT/JP2013/062354.
Sasaki et al, "Catalytic Activities of Isopolytungstate in H2O2-Oxydation of Alcohols and Allyl alcohols," CSJ: The Chemical Society of Japan Koen Yokoshy, vol. 75, p. 287 (1998).
Okovytyy et al, "Identification of the stereoisomers of tetrahydroindene diepoxide by the 1H and 13C NMR characteristics: A combined experimental and theoretical study," Journal of Molecular Structure: THEOCHEM, vol. 730, No. 1-3, pp. 125-132 (2005).
Matoba et al, "Epoxidation of cyclic diolefins with hydrogen peroxide catalyzed by areneseleninic acid," Journal of Japan Petroleum Institute, vol. 26, No. 5, pp. 349-354 (1983).

* cited by examiner

*Primary Examiner* — T. Victor Oh
(74) *Attorney, Agent, or Firm* — Panitch Schwarze Belisario & Nadel LLP

(57) ABSTRACT

In order to produce an epoxy compound with a less chlorine content at a higher reaction rate and yield, the present invention provides a method for producing an epoxy compound by reacting a compound having a carbon-carbon double bond with hydrogen peroxide in the coexistence of the compound having a carbon-carbon double bond, the hydrogen peroxide solution, a powdered solid catalyst support and a powdered solid catalyst all together, the solid catalyst comprising isopolyacids produced from (a) tungstic acid or a salt thereof and (b) a quaternary ammonium salt compound and/or a pyridinium salt, selected from halogen-free compounds.

15 Claims, No Drawings

METHOD FOR PRODUCING EPOXY COMPOUND

CROSS-REFERENCE TO RELATED APPLICATION

This application is a Section 371 of International Application No. PCT/JP2013/062354, filed Apr. 26, 2013, which was published in the Japanese language on Nov. 28, 2013, under International Publication No. WO 2013/175935 A1, and the disclosure of which is incorporated herein by reference.

TECHNICAL FIELD

The present invention relates to a method for producing epoxy compounds from compounds having a carbon-carbon double bond and hydrogen peroxide.

BACKGROUND ART

Epoxy compounds are reacted with various curing agents and curing catalysts to produce cured products. These epoxy compounds are useful as components of coating agents, adhesives, inks or sealants or intermediates for producing compounds which are useful in the various final applications such as pharmaceutical agents or medical products, and it has thus been desired to develop a method for supplying such epoxy compounds which is efficient and environmentally-friendly as well as industrially valuable.

The main component of an epoxy resin that is industrially applicable is produced through a reaction of polyphenols and epichlorohydrin. Glycidyl compounds generated thereupon contain several thousand ppm of chemically bonded chlorine depending on the processing conditions. Chlorine-free epoxy resins have been desired in viewpoint of for example environmental issues or safety. In use for electronic materials in particular, chlorine has been regarded as problems because it causes corrosion of wiring or deterioration of insulating characteristics, resulting in the materials with less reliability, and therefore also in this regard, the epoxy compounds have been demanded to be decreased in the chlorine content.

As a method for producing an epoxy compound, a method is known, in which olefins are oxidized with peracids such as peracetic acid. However, this method has problems that peracids require careful handling, and epoxides are reacted with carboxylic acids presented in the reaction system thereby producing esters and the like, resulting in a decrease in the selectivity of the epoxides, and also that in production of an alicyclic epoxy compound regarded as having a high reactivity with acids, coexisting organic acids are easily reacted with epoxy groups produced in the presence of water, resulting in a decrease in the selectivity of the epoxides due to the ring-opening of the epoxy groups, and the post-treatments are troublesome. Therefore, a method has been attracting attention, which uses hydrogen peroxide as an oxidation agent, which is easy in handling and turns to water that is harmless after the reaction.

As a method for producing an epoxy compound from olefins using hydrogen peroxide, a method is known in which epoxidation is carried out by reacting olefins and a hydrogen peroxide solution with a halogenated hydrocarbon as a solvent using a catalyst such as polyacids (Patent Literature 1). This method, however, has problems concerning halogen impurities in the products and environmental load due to the use of the halogenated hydrocarbon.

Patent Literature 2 discloses a solid phase reaction system for oxidation comprising a mixture of a powdered solid catalyst support and a powdered solid catalyst for oxidation reaction, an organic compound and a hydrogen peroxide solution.

CITATION LIST

Patent Literature

Patent Literature 1: Japanese Patent Application Laid-Open Publication No. 62-234550
Patent Literature 2: WO2008/093711

SUMMARY OF INVENTION

Technical Problem

The present invention has an object to provide a method for producing an epoxy compound with a less chlorine content from a compound having a carbon-carbon double bond and hydrogen peroxide.

Solution to Problem

The present invention relates to a method for producing an epoxy compound by reacting a compound having a carbon-carbon double bond with hydrogen peroxide in the coexistence of the compound having a carbon-carbon double bond, the hydrogen peroxide solution, a powdered solid catalyst support and a powdered solid catalyst all together, the solid catalyst comprising isopolyacids produced from (a) tungstic acid or a salt thereof and (b) a quaternary ammonium salt compound and/or a pyridinium salt, selected from halogen-free compounds.

The present invention also relates to the foregoing method for producing an epoxy compound wherein the tungstic acid or salt thereof is an ammonium tungstate.

The present invention also relates to the foregoing method for producing an epoxy compound wherein the quaternary ammonium salt compound is a salt of cetyltrimethylammonium and, the pyridinium salt compound is a salt of cetylpyridinium.

The present invention also relates to the foregoing method for producing an epoxy compound wherein the epoxy compound is an alicyclic epoxy compound.

The present invention also relates to the foregoing method for producing an epoxy compound wherein the epoxy compound is a compound represented by formula (1):

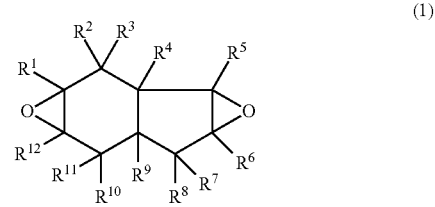

(1)

wherein $R_1$ to $R_{12}$ are each hydrogen, halogen, an alkyl group optionally having halogen or an alkoxy group optionally having a substituent.

The present invention also relates to the foregoing method for producing an epoxy compound wherein the solid catalyst support is selected from the group consisting of phosphates, diatomaceous earth, silica, alumina, kaolin, silica-alumina and calcium fluoride and particularly relates to the foregoing method for producing an epoxy compound wherein the solid catalyst support is apatite.

Advantageous Effect of Invention

The method for producing an epoxy compound of the present invention can produce an epoxy compound with a less chlorine content at a high reaction rate and yield and particularly can provide a highly reliable material for electronic material applications. Furthermore, the method of the present invention has advantages that it can reduce environmental loads caused by wastewater or organic solvents and can reuse the catalyst. The method of the present invention also has features that the solid catalyst and solid catalyst support constituting the solid phase can be reused by simply drying them after removal of the product so that no step making the reaction operation complicated is required upon reuse of the catalyst and isolation or recovery of the product is easily carried out, and thus is a method for producing an epoxy compound with a high industrial value.

DESCRIPTION OF EMBODIMENTS

Preferable embodiments of the present invention will be described below.

The present invention is a method for producing an epoxy compound by reacting a compound having a carbon-carbon double bond with hydrogen peroxide in the coexistence of the compound having a carbon-carbon double bond, the hydrogen peroxide solution, a powdered solid catalyst support and a powdered solid catalyst all together, the solid catalyst comprising isopolyacids produced from (a) tungstic acid or a salt thereof and (b) a quaternary ammonium salt compound and/or a pyridinium salt, selected from compound halogen-free compounds.

That is, the present invention intends to produce an epoxy compound with a less chlorine content using a solid catalyst comprising isopolyacids produced from tungstic acid or a halogen-free salt thereof, a halogen-free quaternary ammonium salt compound and/or a halogen-free pyridinium salt compound.

Specific examples of (a) tungstic acid or a salt thereof used in the present invention include $H_2WO_4$, $Na_2WO_4$, $NaHWO_4$, $(NH_4)_2WO_4$, $(NH_4)HWO_4$, $(NH_4)_{10}[H_2W_{12}O_{42}]$, $[WO(O_2)_2(H_2O)_2]$, $K_2[WO(O_2)_2(H_2O)_2]_2O$ and $Na_2[WO(O_2)_2(H_2O)_2]_2O$. Preferred are ammonium tungstates such as $(NH_4)_{10}[H_2W_{12}O_{42}]$.

Specific examples of (b) the quaternary ammonium salt compound used in the present invention include hydroxides, nitrates, sulfates, hydrogen sulfates, acetates, methosulfates and ethosulfates of tetraalkylammoniums such as benzyltrimethylammonium, benzyltriethylammonium, benzyltributylammonium, phenyltrimethylammonium, tetrabutylammonium, tetrahexylammonium, tetraoctylammonium, trioctylmethylammonium, trioctylethylammonium, dilauryldimethylammonium, lauryltrimethylammonium, distearyldimethylammonium, stearyltrimethylammonium, dioctadecyldimethylammonium, octadecyltrimethylammonium, dicetyldimethylammoniun, cetyltrimethylammonium and tricaprylmethylammonium. Alternatively, the quaternary ammonium salt compound may be any of the organic ammonium salts in the above specific examples that are prepared from naturally-occurring raw materials and having partially in their alkyl group an unsaturated bond or a carbon number distribution. Preferred are cetyltrimethylammonium salts.

Specific examples of (b) the quaternary pyridinium salt compound used in the present invention include hydroxides, nitrates, sulfates, hydrogen sulfates, acetates, methosulfates and ethosulfates of dodecylpyridinium and cetylpyridinium. Preferred are cetylpyridinium salts.

The solid catalyst used in the present invention can be produced by dissolving (a) tungstic acid and (b) a quaternary ammonium salt compound and/or pyridinium salt compound in a solvent such as water to be mixed and reacted and allowing the intended salt that is insoluble in the solvent to precipitate, followed by isolation and purification thereof.

No particular limitation is imposed on the compound having a carbon-carbon double bond used in the present invention if it is a compound having one or more carbon-carbon double bond.

Examples of such a compound include monosubstituted olefins such as ethylene, propylene, 1-butene, 1-pentene, 4,4-dimethyl-1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-octadecene, 3,3-dimethyl-1-butene, vinylcyclopentane, vinylcyclohexane, allylcyclohexane, styrene, 4-(tert-butyl)styrene, allylbenzene, 4-methoxystyrene, safrole, eugenol, and 3,4-dimethoxy-1-allylbenzene;

disubstituted olefins such as 2-butene, isobutylene, 2-methyl-1-butene, 2-pentene, 2-hexene, 2-methyl-1-hexene, 3-hexene, 2-heptene, 2-methyl-1-heptene, 3-heptene, 2-octene, 3-octene, 4-octene, 2-nonene, 2-methyl-2-nonene, 3-nonene, 4-nonene, 5-decene, 2-methyl-1-undecene, cyclopentene, cyclohexene, 4-methylcyclohexene, cycloheptene, cyclooctene, cyclodecene, cyclododecene, methylenecyclohexane, β-methylstyrene, stilbene, isosafrole, isoeugenol, β-pinene and norbornene;

trisubstituted olefins such as 2-methyl-2-butene, 2-methyl-2-pentene, 2-methyl-2-hexene, 2,5-dimethyl-2,4-hexadiene, 2-methyl-2-heptene, 1-methylcyclopentene, 1-methylcyclohexene, 1-(tert-butyl)cyclohexene, 1-isopropylcyclohexene, 2-carene, 3-carene and α-pinene; and tetrasubstituted olefins such as 2,3-dimethyl-2-butene and 2,3,4-trimethyl-2-pentene.

In the present invention, other than the above-described olefin compounds, alicyclic olefin compounds represented by formula (2) below are also preferably used as the compound having a carbon-carbon double bond. In this case, an alicyclic olefin compound represented by formula (2) is epoxylated thereby producing an alicyclic epoxy compound represented by formula (1) below.

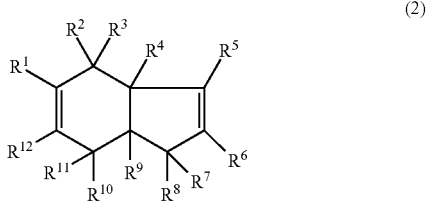

(2)

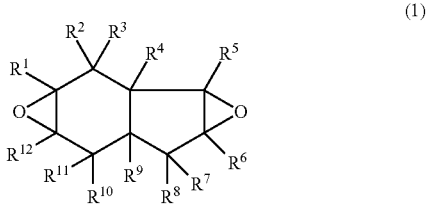

(1)

In formulas (1) and (2), $R_1$, $R_2$, $R_3$, $R_4$, $R_5$, $R_6$, $R_7$, $R_8$, $R_9$, $R_{10}$, $R_{11}$ and $R_{12}$ are each independently hydrogen, halogen, an alkyl group which may have a substituent or an alkoxy group which may have a substituent.

The alkyl group is preferably an alkyl group having 1 to 10 carbon atoms, more preferably an alkyl group having 1 to 4 carbon atoms. When the alkyl group has a substituent, examples thereof include halogens and alkoxy groups.

The alkoxy group is preferably an alkoxy group having 1 to 10 carbon atoms, more preferably an alkoxy group having 1 to 4 carbon atoms. when the alkoxy group has a substituent, examples thereof include halogens and alkoxy groups.

$R_1$ to $R_{12}$ are each independently preferably, hydrogen, fluorine, an alkyl group or an alkoxy group, more preferably hydrogen or fluorine, more preferably hydrogen.

That is, the alicyclic olefin compound represented by formula (2) is preferably a compound represented by formula (4) below from which an alicyclic diepoxy compound represented by formula (3) below can be produced through oxidation reaction.

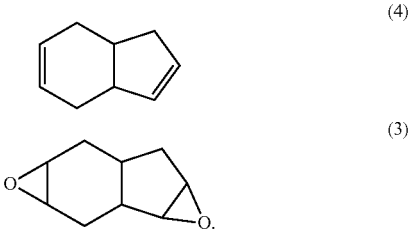

(4)

(3)

The solid catalyst support may be powders of solid materials having properties that they disperse a solid catalyst, a hydrogen peroxide solution and a compound having a carbon-carbon double bond, are not degraded thereby and do not disturb the oxidation reaction, preferably those having properties to facilitate the oxidation reaction. Specific examples include phosphates such as apatite, clays such as diatomaceous earth [main component: silica], kaolin [main component: silica-alumina] and hydrotalcite, fluorides such as calcium fluoride, and oxides such as silica, titania and alumina. Among these, a solid catalyst support selected from phosphates, diatomaceous earth, silica, alumina, kaolin, silica-alumina and calcium fluoride is preferably used because they can achieve a higher yield. In particular, a solid catalyst support selected from apatite, diatomaceous earth and calcium fluoride can achieve a particularly higher yield.

Herein, the apatite is a kind of calcium phosphate, and fluorapatite, chlorapatite, carbonate apatite and hydroxyapatite exist as apatite-type minerals. Among these, hydroxyapatite and fluorapatite are preferably used.

The diatomaceous earth is a soft rock or soil composed mainly of a husk of Bacillariophyta, and contains silica as a main component but also often alumina, ferric oxide, alkali metal oxides in addition to silica. Alternatively, those which are porous and have a high porosity and a cake bulk density of about 0.2 to 0.45 are often used. Among diatomaceous earths, calcined products or freshwater diatomaceous earths are preferred but other diatomaceous earths may be used. Specific examples of such diatomaceous earths include those marketed under the tradename of Celite (registered trademark) by Celite Corporation and marketed under the tradename of Celatom by Eagle Pitcher Minerals, Inc. Alternatively, those calcined together with sodium carbonate may also be used.

The solid catalyst is not required to be immobilized to the solid catalyst support, and all what needs to be done is that the powdered solid catalyst is simply mixed with the powdered solid catalyst support. For example, the powdered solid catalyst is added in advance to the powdered solid catalyst support and then stirred and mixed thereby producing a mixture of the solid catalyst and solid catalyst support. No particular limitation is imposed on the particle sizes of the powdered solid catalyst and powdered solid catalyst support. Those having a particle size of about 5 to 100 μm, which are easily available may be used thereby achieving the advantageous effects of the present invention such as a higher yield of the product.

The amount of the solid catalyst is preferably 5 to 60 percent by mass, more preferably 10 to 50 percent by mass of the solid catalyst support. With 5 percent by mass or less of the catalyst, the compound represented by formula (1) cannot be produced at a high yield because the reaction rate is decreased. With more than 60 percent by mass of the catalyst, the yield cannot be improved, and thus it is industrially disadvantageous.

Next, to the mixture of the powdered solid catalyst support and the powdered solid catalyst produced as described above are added a compound having a carbon-carbon double bond to be oxidized and a hydrogen peroxide solution. This addition is so carried out that both of them are dispersed in the above-described mixture and come into mutual contact. For example, they may be mixed, stirring so that they are dispersed and come into mutual contact well. Thereafter, they may be reacted, allowing to stand or alternatively mixed and stirred.

The hydrogen peroxide solution may be used in an amount of about 1 to 10 mmol as hydrogen peroxide of 1 mmol of the double bond site of the compound having a carbon-carbon double bond, but the amount is desirously from 1.2 to 5 mmol. Less than 1 mmol of the hydrogen peroxide solution results in lack of hydrogen peroxide while more than 10 mmol of the hydrogen peroxide solution results in a decrease in the yield of an epoxy compound due to ring-opening of the epoxides. In particular, in the case of producing a compound represented by formula (1), the yield thereof would tend to be decreased.

The solid catalyst support and solid catalyst may be used in an amount of about 0.01 to 5 g on the basis of 1 mmol of the compound having a carbon-carbon double bond but desirously used in an amount of 0.05 to 3.0 g.

In the present invention, the hydrogen peroxide solution is used at a concentration of preferably 5 to 60 percent by mass, more preferably 5 to 35 percent by mass. In the case of using a hydrogen peroxide solution of a low concentration in a method for producing an epoxy compound using hydrogen peroxide, the produced epoxide is hydrolyzed to produce by-products such as diols and the like, resulting in the reduced selectivity of the intended product. However, the method of the present invention is high in selectivity and can produce the intended product at a higher yield even in the case of using a hydrogen peroxide solution of low concentration.

Handling of a hydrogen peroxide solution at a concentration of 35 to 60 percent by mass involves danger to an extent that transportation thereof is regulated, and a two phase heterogeneous reaction system requires some reaction equipment that can sufficiently avoid the occurrence of rapid exothermic reaction or explosion. However, the method of the present invention enables the reaction to be carried out more safely with a practical yield of the product by impregnating the solid phase with a hydrogen peroxide solution.

An organic solvent may be further added to the mixture of the powdered solid catalyst support and powdered solid catalyst before, after or simultaneously with adding thereto the compound having a carbon-carbon double bond and the hydrogen peroxide solution. The use of the organic solvent can restrain epoxides and water from contacting mutually so as to be likely to avoid the produced epoxides from ring-opening. The organic solvent is added in an amount of 0 to 500 percent by mass on the basis of the compound having a carbon-carbon double bond. More than 500 percent by mass of the organic solvent causes the reaction rate to reduce and thus causes the yield of an epoxy compound to decrease.

Examples of the organic solvent include alcohols, ethers, esters, ketones, nitrile, amides, sulfones, epoxides, aliphatic compounds, aromatic compounds and the like. The organic solvent is preferably ethanol, ethyl acetate, hexane or toluene, particularly preferably toluene.

In the present invention, the oxidation reaction temperature is preferably from 0 to 50° C., more preferably 5 to 40° C. At lower than 0° C., the reaction proceeds slowly while at higher than 50° C., it causes the yield to decrease due to deactivation of the solid catalyst or ring-opening of the epoxides.

The reaction time is generally preferably from 1 to 24 hours, more preferably 1 to 12 hours. With a reaction time of shorter than 1 hour, the reaction does not proceed sufficiently and thus decreases the yield while with a reaction time of longer than 24 hours, the productivity decreases.

In the present invention, the conversion rate of olefin compounds is preferably 80% or greater, and the yield of an epoxy compound is preferably 50% or greater.

No particular limitation is imposed on the method for isolating the produced epoxy compound. For example, a method may be used wherein the epoxy compound is solvent-extracted and then concentrated.

The chlorine content of the epoxy compound produced by the present invention is preferably 100 ppm by mass or less, more preferably 10 ppm by mass or less because the compound when formed into a cured resin product can be further improved in moisture proof reliability. The chlorine content is the value measured in accordance with JIS K-7243-3, specifically the value measured by dissolving an epoxy compound in diethylene glycol monobutyl ether and saponifying the solution with a potassium hydroxide alcohol solution, heating it to reflux, followed by potentiometric titration with a silver nitrate solution.

The chlorine content of the epoxy compound can be reduced by purification by distillation, or alternatively by a method such as alkali aqueous solution washing or absorbent treatment.

The metal content of the epoxy compound produced by the present invention is preferably 100 ppm by mass or less, more preferably 10 ppm by mass or less because a cured resin product produced from the compound is further enhanced in mechanical characteristics and electrical characteristics. The metal content can be measured by analyzing a 10% toluene solution of an epoxy compound with inductively-coupled plasma emission (ICP emission). The apparatus for the measurement may be Optima 4300DV manufactured by Perkin-Elmer Corp. In this measurement, quantitative analysis of each metal species detected by qualitative analysis can be carried out using a commercially available metal standard solution.

The metal content of the epoxy compound can be reduced by purification by distillation, or alternatively by a method such as alkali aqueous solution washing or absorbent treatment.

EXAMPLES

The present invention will be described in more detail with the following examples but is not limited thereto.

Example 1

Ammonium paratungstate tetrahydrate was added in an amount of 16 g (5.0 mmol) to 650 ml of water and then dissolved by heating the mixture to 65° C. Cetyltrimethylammonium methosulfate was added in an amount of 16 g (40 mmol) to 250 ml of water and dissolved by heating the mixture to 35° C. The ammonium paratungstate aqueous solution was added to the cetyltrimethyl ammonium methosulfate aqueous solution, stirring at room temperature and then further stirred at room temperature for 30 minutes. The white suspension thus produced was filtered and then washed with 700 ml of water. The resulting white solid was dried at room temperature under reduced pressure thereby producing 24 g of Catalyst A. Catalyst A had a total chlorine content of less than 10 ppm by mass.

Into a screw-top test tube were weighed out 0.50 g of apatite that is a solid catalyst support and 0.074 g (0.015 mmol) of Catalyst A that is a solid catalyst, followed by well-mixing. To the mixture were added 0.12 g (1.0 mmol) of tetrahydroindene and 0.23 g (2.4 mmol) of a 35% hydrogen peroxide solution, followed by well-stirring. Thereafter, the mixture was allowed to stand at 15° C. After the mixture was allowed to stand at 15° C. for 3 hours, the resulting reaction mixture was extracted with hexane (5 mL×3 times) and the solvent was distilled out from the extracted solution thereby producing 0.15 g of a crude product. The crude product was distilled at 60 Pa and a bottom temperature of 80° C. thereby producing 0.14 g of tetrahydroindene diepoxide, which was a colorless transparent solution. The yield of the product (diepoxide yield) was 95%. The product had a total chlorine content of 10 ppm by mass.

Comparative Example 1

Ammonium paratungstate tetrahydrate was added in an amount of 16 g (5.0 mmol) to 650 ml of water and then dissolved by heating the mixture to 65° C. Cetylpyridinium chloride monohydrate was added in an amount of 16 g (45 mmol) to 250 ml of water and dissolved by heating the mixture to 35° C. The ammonium paratungstate aqueous solution was added to the cetylpyridinium chloride aqueous solution, stirring at room temperature and then further stirred at room temperature for 30 minutes. The white suspension thus produced was filtered and then washed with 700 ml of water. The resulting white solid was dried at room temperature, under reduced pressure thereby producing 27 g of Catalyst B. Catalyst B had a total chlorine content of 940 ppm by mass.

Into a screw-top test tube were weighed out 0.50 g of apatite that is a solid catalyst support and 0.085 g (0.015 mmol) of Catalyst B that is a solid catalyst, followed by well-mixing. To the mixture were added 0.12 g (1.0 mmol) of tetrahydroindene and 0.23 g (2.4 mmol) of an 35% hydrogen peroxide solution, followed by well-stirring. Thereafter, the mixture was allowed to stand at 15° C. After the mixture was allowed to stand at 15° C. for 3 hours, the reaction mixture was extracted with hexane (5 mL×3 times) and the solvent was distilled out from the extracted solution thereby producing 0.15 g of a crude product. The crude product was distilled at 60 Pa and a bottom temperature of 80° C. thereby producing 0.14 g of tetrahydroindene diepoxide, which was a colorless transparent solution. The yield of the product (diepoxide yield) was 95%. The product had a total chlorine content of 126 ppm by mass.

INDUSTRIAL APPLICABILITY

The present invention can produce a highly industrially valuable epoxy compound with a less chlorine content at a higher reaction rate and a higher yield.

The invention claimed is:

1. A method for producing an epoxy compound with a low chlorine content by reacting a compound having a carbon-carbon double bond with hydrogen peroxide in the coexistence of the compound having a carbon-carbon double bond, the hydrogen peroxide solution, a powdered solid catalyst support and a powdered solid catalyst all together, the solid catalyst comprising isopolyacids produced from (a) tungstic acid or a salt thereof and (b) a quaternary ammonium salt compound and/or pyridinium salt compound, selected from chlorine free compounds, wherein the chlorine content of the epoxy compound is 100 ppm by mass or less.

2. The method for producing an epoxy compound according to claim 1 wherein (a) the tungstic acid or salt thereof is an ammonium tungstate.

3. The method for producing an epoxy compound according to claim 1 wherein (b) the quaternary ammonium salt compound is a salt of cetyltrimethyl ammonium, and (b) the pyridinium salt compound is a salt of cetylpyridinium.

4. The method for producing an epoxy compound according to claim 1 wherein the epoxy compound is an alicyclic epoxy compound.

5. The method for producing an epoxy compound according to claim 1 wherein the epoxy compound is a compound represented by formula (1):

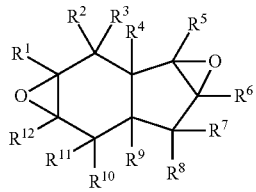

(1)

wherein $R^1$ to $R^{12}$ are each hydrogen, halogen, an alkyl group optionally having halogen or an alkoxy group optionally having halogen or an alkoxy group as a substituent.

6. The method for producing an epoxy compound according to claim 1 wherein the solid catalyst support is selected from the group consisting of phosphates, diatomaceous earth, silica, alumina, kaolin, silica-alumina and calcium fluoride.

7. The method for producing an epoxy compound according to claim 1 wherein the solid catalyst support is apatite.

8. The method for producing an epoxy compound according to claim 1 wherein a chlorine content in the solid catalyst is less than 10 ppm by mass.

9. The method for producing an epoxy compound according to claim 1 wherein the chlorine content of the epoxy compound is 10 ppm by mass or less.

10. The method for producing an epoxy compound according to claim 1 wherein the isopolyacid is a compound produced from (a) an ammonium tungstate and (b) a salt of cetyltrimethyl ammonium.

11. A method for producing an epoxy compound with a chlorine content of 100 ppm by mass or less by reacting a compound represented by formula (2) below with hydrogen peroxide in the coexistence of the compound represented by formula (2) below, the hydrogen peroxide solution, a powdered solid catalyst support and a powdered solid catalyst comprising isopolyacids produced from (a) an ammonium tungstate and (b) a salt of cetyltrimethyl ammonium,

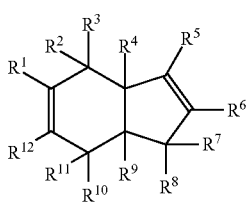

(2)

wherein $R^1$ to $R^{12}$ are each hydrogen, halogen, an alkyl group optionally having halogen or an alkoxy group optionally having halogen or an alkoxy group as a substituent.

12. The method for producing an epoxy compound according to claim 11 wherein a chlorine content in the solid catalyst is less than 10 ppm by mass.

13. The method for producing an epoxy compound according to claim 11 wherein the chlorine content of the epoxy compound is 10 ppm by mass or less.

14. The method for producing an epoxy compound according to claim 11 wherein the solid catalyst support is selected from the group consisting of phosphates, diatomaceous earth, silica, alumina, kaolin, silica-alumina and calcium fluoride.

15. The method for producing an epoxy compound according to claim 11 wherein the solid catalyst support is apatite.

* * * * *